United States Patent
Bayerl et al.

(10) Patent No.: US 7,175,747 B2
(45) Date of Patent: Feb. 13, 2007

(54) METHOD FOR ELECTROPHORETICALLY SEPARATING MEMBRANE PROTEINS

(76) Inventors: Thomas Bayerl, Würzburg (DE); Erich Sackmann, München (DE)

( * ) Notice: Subject to any disclaimer, the term of this patent is extended or adjusted under 35 U.S.C. 154(b) by 651 days.

(21) Appl. No.: 10/297,214

(22) PCT Filed: Jun. 1, 2001

(86) PCT No.: PCT/EP01/06234

§ 371 (c)(1),
(2), (4) Date: Apr. 28, 2003

(87) PCT Pub. No.: WO01/94421

PCT Pub. Date: Dec. 13, 2001

(65) Prior Publication Data

US 2003/0159933 A1 Aug. 28, 2003

(30) Foreign Application Priority Data

Jun. 3, 2000 (DE) .............................. 100 27 705

(51) Int. Cl.
G01N 27/447 (2006.01)
G01N 27/453 (2006.01)
(52) U.S. Cl. ....................................... 204/450; 204/600
(58) Field of Classification Search ................ 204/450, 204/600
See application file for complete search history.

(56) References Cited

U.S. PATENT DOCUMENTS 4,654,132 A * 3/1987 Takagi et al. ............... 204/468

2001/0025791 A1 * 10/2001 Landau et al. ............... 204/451

FOREIGN PATENT DOCUMENTS

WO WO-91/04326 A1 * 4/1991

OTHER PUBLICATIONS

Xu Chong et al "Two-dimensional electrophoretic profile of human sperm membrane proteins." vol. 15 No. 6, 1994, pp. 595-602.
Stelzle M et al "Two-dimensional microelectrophoresis I supported lipid bilayers." vol. 63, No. 5, 1992, pp. 1346-1354.

* cited by examiner

Primary Examiner—Alex Noguerola
(74) Attorney, Agent, or Firm—Antonelli, Terry, Stout and Kraus, LLP.

(57) ABSTRACT

The one and two-dimensional separation of proteins extending through the membrane (membrane proteins) is a prerequisite for a complete analysis of the proteome of a functionally intact cell organelle. A substantial drawback of prior art methods for separating is that their applicability is limited to peripheral water-soluble proteins. The aim of the novel method is to electrophoretically separate membrane proteins in one or two dimensions. To this end, membranes from cell organelles, whose membrane protein stock should be separated, are placed on planar supports whose surface was modified using suitable methods in such a manner that the membrane proteins maintain their ability to laterally diffuse in the membrane plane after being placed on the support. By subsequently applying electrical fields, the proteins can be electrophoretically displaced in the membrane plane and, as a result, can be separated in one or two dimensions according to their different charge characteristics.

32 Claims, 4 Drawing Sheets

METHOD FOR ELECTROPHORETICALLY SEPARATING MEMBRANE PROTEINS

Figure 1:
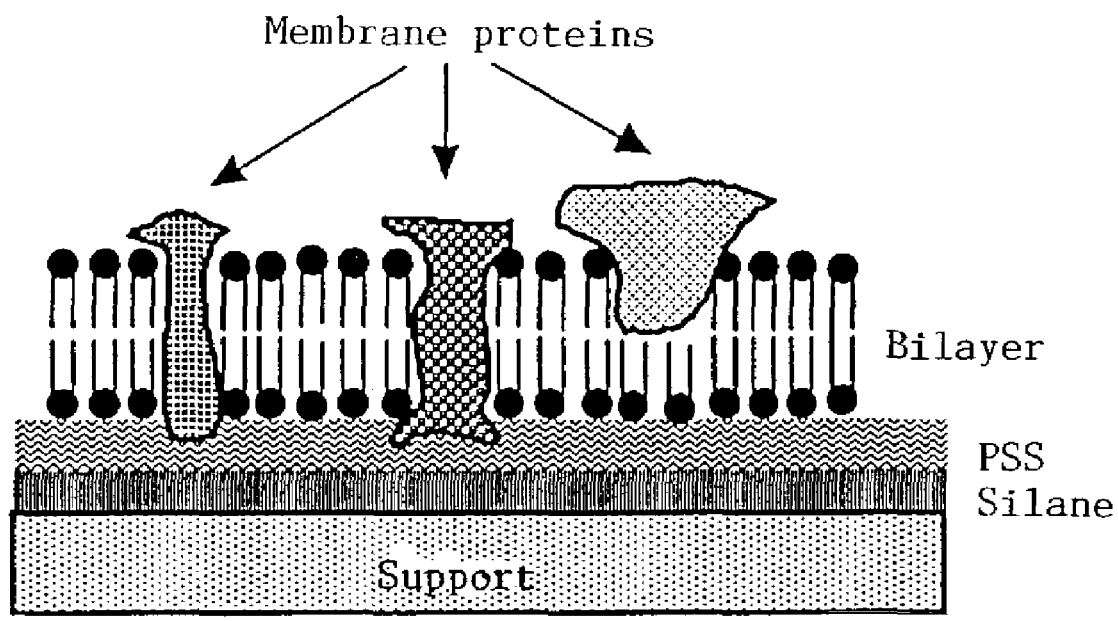

This application is an application filed under 35 USC 371 of international application PCT/EP01/06234, filed Jun. 1, 2001 and designating the U.S.

The two-dimensional separation of proteins is a prerequisite for proteome analysis of cells and has hitherto almost exclusively taken place through two-dimensional polyacrylamide gel electrophoresis (2D-PAGE). The disadvantage of this technology is the insolubility of membrane proteins in the gels used for 2D-PAGE technology. Membrane proteins are here understood to mean those proteins which either extend through the membrane (e.g. ionophores or receptors) or which are embedded at least on one side in the hydrophobic area of the membrane (e.g. surface receptors). Thus, 2D-PAGE technology is unable to separate membrane proteins. However, as for the function of a cell, membrane proteins have a vital significance, proteome analysis based on 2D-PAGE is incomplete.

For overcoming this problem it is a question of finding a matrix capable of electrophoresis, which allows a dissolving of the membrane protein and which also allows the application of ion gradients or pH-gradients for further separation.

Further information is given in the literature and is directed at solving specific 2D-PAGE problems (Wall D. B., Kachman M. T., Gong S. Y., et al. "Isoelectric focusing nonporous RP HPLC: A two-dimensional liquid-phase separation method for mapping of cellular proteins with identification using MALDI-TOF mass spectrometry" Anal. Chem. 72: (6) 1099–1111, 2000; Seehof K., Kresse M., Mader K. et al. "Interactions of nanoparticles with body proteins—improvement of 2D-PAGE analysis by internal standard" Int. J. Pharm. 196: (2) 231–234, 2000), but have been unable to offer satisfactory alternatives for the above-mentioned solubility problem in connection with integral membrane proteins.

In the early 1990s, lipid double layers (hereinafter called bilayers), applied to a planar substrate (so-called solid-supported bilayers) were successfully investigated for their electrophoresis capacity. It was possible to show that the lipids of the bilayer were displaceable in accordance with the electric charge of their top group through an applied electric field within the plane of the bilayer (i.e. in two-dimensional manner) (Stelzle M., Sackmann E., "Sensitive detection of protein adsorption for supported lipid bilayers by frequency-dependent capacitance measurements and microelectrophoresis", Biochim. Biophys. Acta 981, 135–142, 1989; Stelzle M., Miehlich R., Sackmann E. "Two-dimensional microelectrophoresis in supported lipid bilayers", Biophysical Journal 63, 1346–1354, 1992; Groves J. T., Boxer S. G. "Electric field-induced concentration gradients in planar supported bilayers", Biophys. J. 69, 1972–1975, 1995). Further articles have revealed that also the microstructuring of the substrate (usually silicon or silicates) influences the movement and movement direction of the lipids in the electric field (van Oudenaarden A., Boxer S. G., "Brownian ratchets: molecular separations in lipid bilayers supported on patterned arrays", Science, 285, 1046–1048, 1999) and that this movement can set insurmountable barriers for the lipids (Groves J. T., Ulman N., Boxer S. G. "Micropatterning fluid lipid bilayers on solid supports", Science 275, 651–653, 1997).

The use of lipid monolayers (hereinafter called monolayers), which were transferred by Langmuir-Blodgett transfer to planar substrates, in the form of a matrix capable of electrophoresis is also described in the literature and experiments were able to demonstrate the movement of the lipids in the plane of the monolayer through the action of the electric field applied (Dietrich C., Tampé, R. "Charge determination of membrane molecules in polymer-supported lipid bilayers", Biochim. Biophys. Acta 1238, 183–191, 1995).

Hitherto a description has not appeared of the use of lipid-based electrophoresis matrixes for separating membrane proteins. In principle they should be suitable for this, because the lipids in the form of a lipid bilayer represent the natural matrix for membrane proteins and the presence of specific lipids is frequently decisive for the function of the membrane proteins embedded therein.

For lipid monolayers it is immediately apparent that they are unsuitable for such a use, because they only represent half a membrane and consequently cannot provide a functional environment for a membrane protein.

In connection with solid-supported bilayers, essentially two problems have hitherto made it impossible to use these systems as an electrophoresis matrix for membrane proteins.

1) The hitherto described preparation methods for these bilayers are scarcely suitable for incorporating the entire multiplicity of membrane proteins of a cell in a solid-supported bilayer. This has hitherto only been successful for individual membrane proteins through the fusion of so-called proteoliposomes on the substrate surface (Salafsky J., Groves J. T., Boxer S. G. "Architecture and function of membrane proteins in planar supported bilayers: a study with photosynthetic reaction centers", Biochemistry 26, 14773–14781, 1996).

2) Through the close contact of the bilayer with the inorganic substrate surface (the thickness of the water layer between them is max 3 nm) (Johnson S. J., Bayerl T. M., McDermott D. C., Adam G. W., Rennie A. R., Thomas R. K., Sackmann E. "Structure of an adsorbed dimyristoylphosphatidylcholine bilayer measured with specular reflection of neutrons", Biophys. J., 59, 289–294, 1991; Krueger S., Koenig B. W., Orts W. J., Berk N. F., Majkrzak C. F., Gawrisch K. "Neutron reflectivity studies of single lipid bilayers supported on planar substrates", Basic Life Sci. 64, 205–213, 1996) the membrane protein is too close to the substrate surface and can denature or be immobilized thereon. Thus, its movement in the plane of the bilayer is greatly hindered or rendered impossible by external electric fields.

The novel method is intended to obviate these problems and therefore permit for the first time the electrophoresis of the complete stock of membrane proteins of a cell, cell organelles or a tissue of identical cells with a bilayer as the matrix.

The inventive transformation of the novel method takes place in three stages:

a) Performing a suitable chemical modification of the substrate surface with the aim of preventing a direct contact between the membrane protein in the solid-supported bilayer and the substrate and to simultaneously permit a mobility of the membrane protein in the plane of the bilayer applied to the modified surface by external electric fields, pH-gradients or salt gradients.

b) Application of the bilayer to the modified surface in such a way that substantially all the membrane proteins of a cell or cell organelle are transferred and are therefore available for two-dimensional separation.

c) Spatial separation of the membrane proteins by the application of suitable electric fields, pH-gradients or salt gradients in accordance with prior art methods.

The solution of the first stage is achieved by the chemical modification of the surface using prior art methods. In general, this objective can be achieved in two ways: (i) Through the non-specific adsorption of monomers or polymers according to prior art methods (particularly deposition from the solution). (ii) By covalent fixing in accordance with the prior art of the molecule specified in (i) to the substrate surface. The criterion for the choice of the molecules used for (i) and (ii) is the formation of a hydrophilic interface to the bilayer, the spontaneous formation of a bilayer according to prior art methods (particularly vesicle fusion) on said modified surface and the diffusive movement of the bilayer components (particularly the membrane proteins therein) in the plane of the bilayer formed.

The inventive transformation of the second stage takes place through the use of vesicles of natural or transgenetic cell or tissue material for the coating of the surface produced in the first stage with a bilayer. For this purpose the cells are split up by prior art separation methods and separated into their individual organelles. From the suspension of the organelles of interest and using prior art methods vesicles are produced, which are able to spontaneously form a planar bilayer on the modified surface. The methods used for vesicle preparation (particularly the treatment of the membrane material with ultrasonics and extrusion (high pressure filtration) through nanoporous filters) must ensure that the membrane proteins in the membranes are also contained in the vesicles resulting from the treatment.

The result of the successful transformation of these two stages is a planar membrane with a composition of lipids and proteins (including and in particular membrane proteins), largely coinciding with those of the cell material used and whose components have in the bilayer plane a diffusive mobility.

In the third stage, by the application of an electric field in the plane of the bilayer and, if necessary, assisted by additional electrical control fields, whose orientation (electric field vector) can also be located outside said plane, there is a one or two-dimensional separation of the membrane proteins in accordance with their charge and molecule size. Unlike the 2D-PAGE method according to the prior art, the proteins are distributed over the entire planar surface as a result of the described bilayer preparation prior to electric field application. The electric fields to be applied must take account of this fact. A further separation of the membrane proteins is possible through the application of pH-gradients or salt gradients to the bilayer side oriented towards the volume and using prior art methods. An even better separation is possible through the application of separate pH or salt gradients within the chemically modified surface described in the first stage and parallel to the bilayer plane.

Finally, an additional microstructuring or nanostructuring of the substrate used can further improve the separation of the membrane proteins with the above-described methods. This possibility for lipids in solid-supported bilayers constitutes prior art.

A further analysis of the one or two-dimensionally separated proteins is possible in that after electrophoresis, removal takes place from the aqueous phase in which it was previously embedded of the support with the membrane. This can e.g. take place through a rapid drying of support and membrane, which almost completely prevents further diffusion of the membrane components (lipids and proteins). Thus, the separation obtained through electrophoresis is fixed and a return to the initial state is no longer possible. The further analysis can take place by suitable high detection sensitivity methods according to the prior art (particularly fluorescence and luminescence detection, as well as radioactive detection of the previously correspondingly labelled membrane proteins).

In the drawings show:

FIG. 1 A diagrammatic representation (side view) of the solid-supported membrane used for electrophoresis and located on a modified support, the complete membrane being located in a not shown buffer solution.

Figure 2:
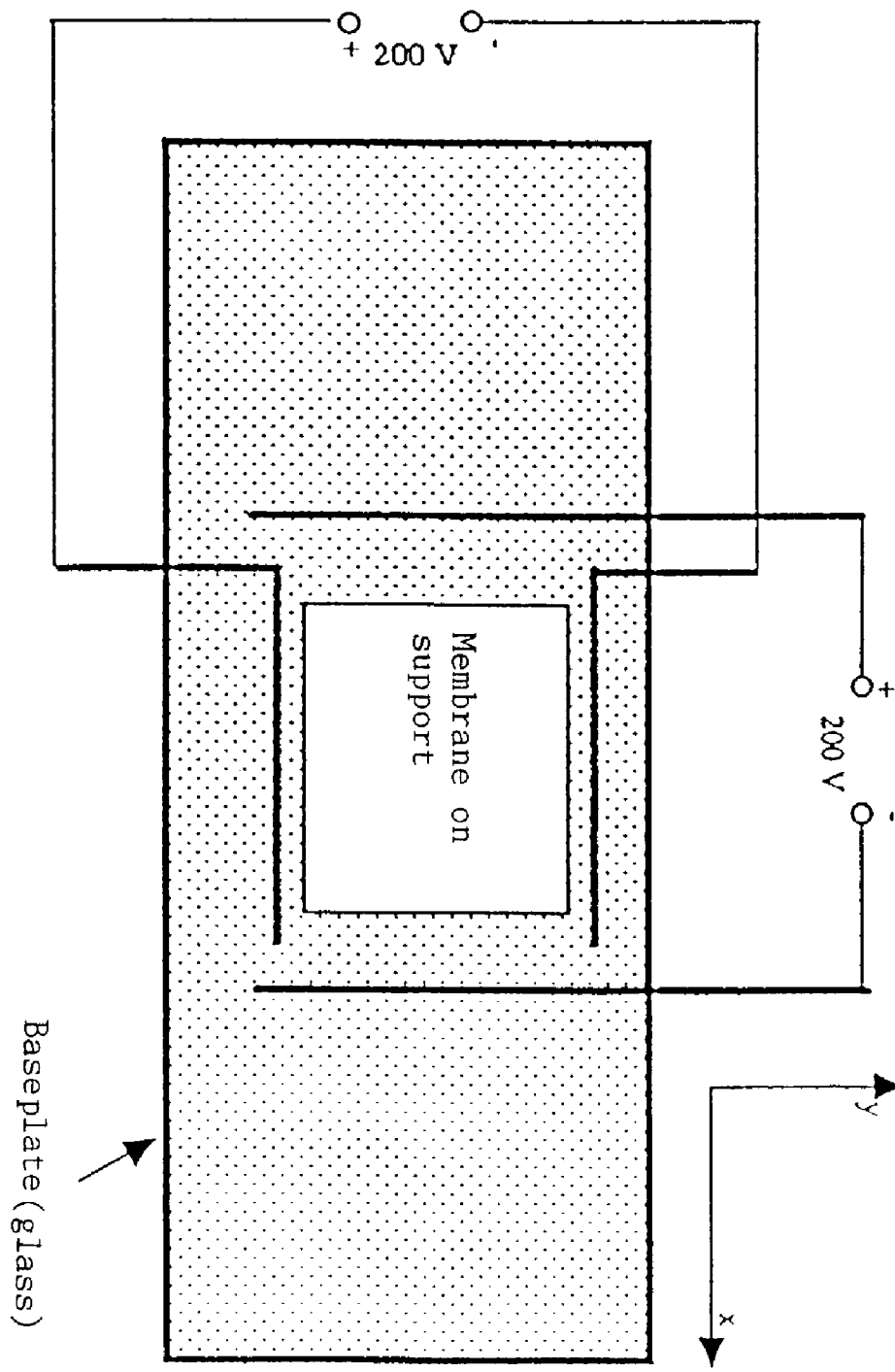

FIG. 2 A diagrammatic representation (plan view) of the measuring setup used for performing membrane protein electrophoresis. The membrane shown in FIG. 1 is located in the centre between the four electrodes. The chamber which can be mounted from above is not shown and is used for the watertight sealing of the setup and has nozzles or pipe lengths for filling with buffer solution.

Figure 3:
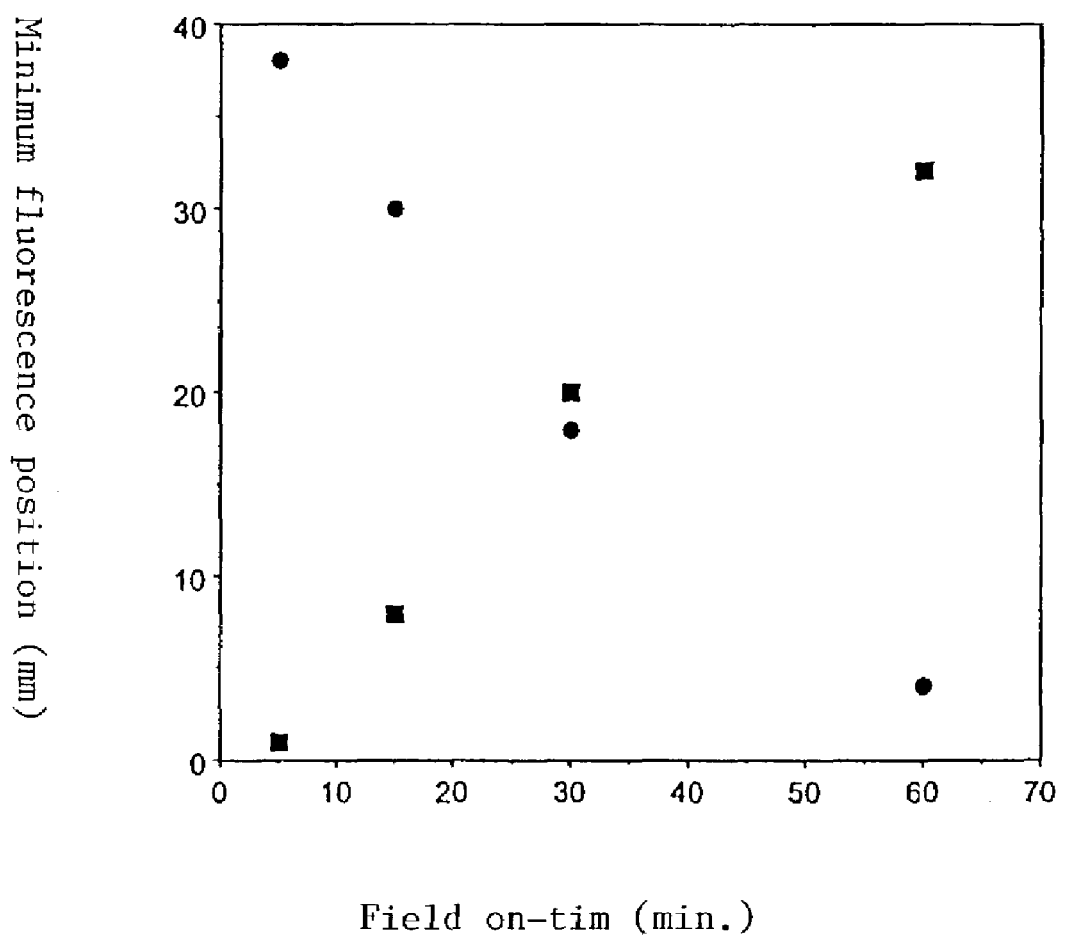

FIG. 3 The dependence of the position of the fluorescence minimum of glycophorine (squares) and band-3 protein (circles) between the electrodes (x-direction) on the duration of the on-time $t_e$ of an electric field with a strength of 200 V/cm according to example 3.1.

Figure 4:
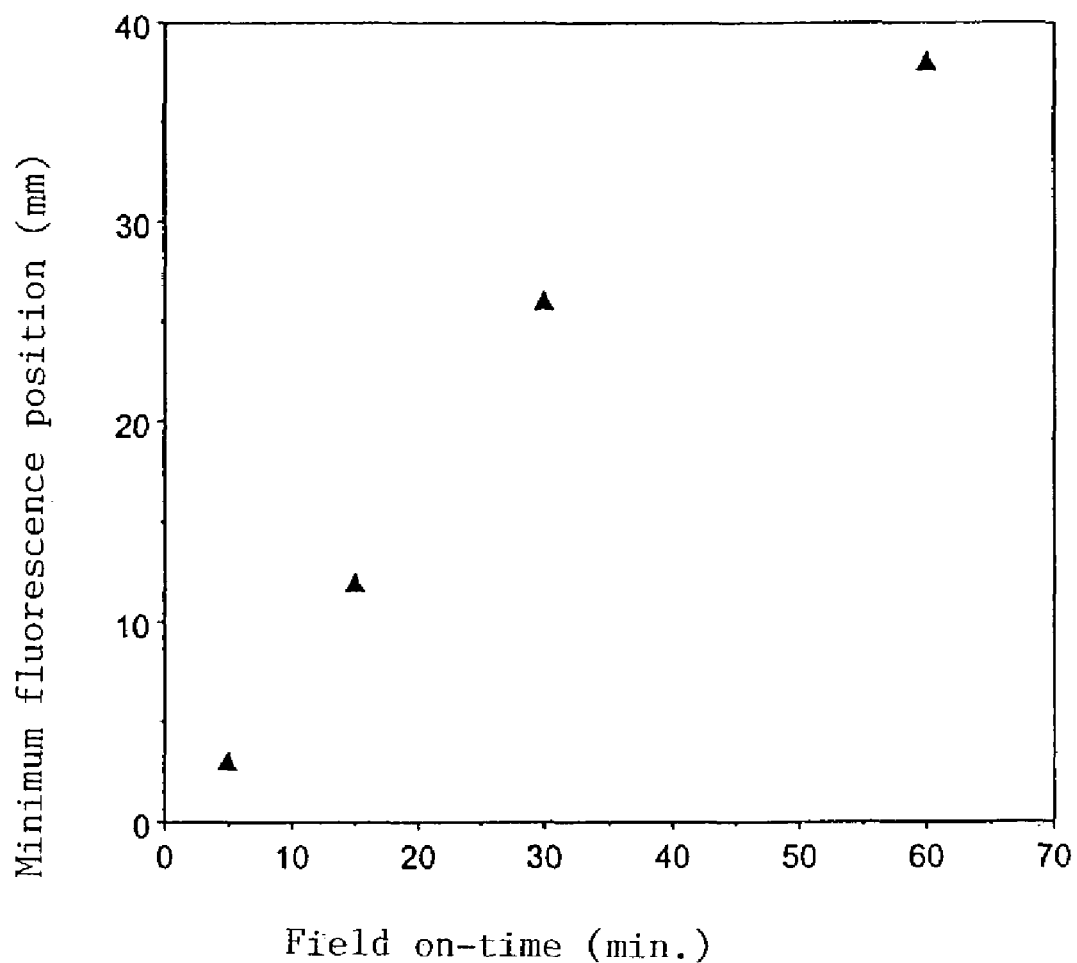

FIG. 4 Dependence of the position of the fluorescence minimum of calcium ATP-ase of the sarcoplasmic reticulum between the electrodes (x-direction) on the duration of the on-time $t_e$ of an electric field with a strength of 200 V/cm according to example 3.2.

EXAMPLES

1. Modification of Solid Surfaces

An amino-modification of a slide with aminopropyl trimethoxysilane (EDA) and subsequent coating with polystyrene sulphonate (PSS) was carried out in the following way. A glass slide for microscopy purposes and of dimensions 20×20 mm was completely immersed in a freshly prepared silane solution consisting of 0.5 ml EDA and 14 µl concentrated acetic acid in 50 ml of deionized water. The modified substrate was then rinsed three times with deionized water and kept for one hour at 80° C. The wetting behaviour changed after silanizing the substrate. The success of the treatment was documented by contact angle measurements using prior art methods.

The glass substrate was then immersed for 30 minutes in a Na-polystyrene sulphonate (PSS) solution consisting of 12.5 mg PSS in 25 ml of deionized water. The modified substrate was then rinsed three times with deionized water and dried. The success of the polymer adsorption was documented by FTIR spectroscopy in the reflection mode.

2. Application of a Natural Membrane to the Modified Surface 2.1 Erythrocyte Membrane Using human erythrocytes so-called "right-side-out" vesicles (Ery-RSO vesicle) were prepared according to Steck T. L., Weinstein R. S. and Wallach D. F. H., "Inside-Out Red Cell Membrane Vesicles: Preparation and Purification", Science, 168, 1970, 255–257. The Ery-RSO vesicles were dispersed in a 5 mM PBS buffer, pH 8.0 (5 mM $N_2HPO_4$, 5 mM $NH_2PO_4$) (hereinafter called buffer B) and then transferred by pressure filtration (extrusion) through polycarbonate membranes (100 nm pore diameter) into small, single-shell vesicles with a diameter of 20 to 90 nm. The slide modified in accordance with 1 was added to 2 ml of this solution (0.5 mg total protein content) in an incubation vessel and incubated for 5 hours accompanied by slight shaking. The support was then washed three times with buffer B. The success of the coating was documented by infrared spectroscopy in reflection. A diagrammatic representation of the arrangement of the membrane on the support appears in FIG. 1.

2.2. Membrane of the Sarcoplasmic Reticulum

Using the method of W. Hasselbach and M. Makinose (Biochem. Z. 1961, 333, 518–528), from the muscular tissue of a rabbit membrane vesicles of the sarcoplasmic reticulum were prepared (SR-vesicles) and dispersed in a buffer of 100 mM of triethanol amine (pH=7.4) and 100 mM NaCl (buffer C). This dispersion was subsequently transformed by ultrasonic treatment into small, single shell vesicles with a diameter of 20 to 90 nm. The slide modified according to 1 was added to 2 ml of this solution ( 0.5 mg total protein content) in an incubation vessel and incubated for 5 hours, accompanied by slight shaking. The support was then washed three times with buffer C. The success of the coating was documented by infrared spectroscopy in reflection.

3. Electrophoresis (One-Dimensional)

3.1. Erythrocyte Membrane

The erythrocyte membrane prepared according to 2.1 was placed in the measuring chamber of a fluorescence microscope. Two platinum wire electrode pairs were fitted to the base plate (glass) of the measuring chamber in such a way that electric fields could be switched both in the x-direction and in the y-direction (FIG. 2). The prepared membrane was fixed to the base plate between the two electrode pairs. A Teflon cover with a glass window sealed in watertight manner to the outside by means of an O-ring said area, including the electrodes, so that the membrane was completely surrounded by buffer A. Thermostatting of the measuring chamber throughout the experiment ensured a constant temperature of 25° C. Inlets and outlets in the fittable cover of the measuring chamber made it possible to flush in buffer and molecules dissolved therein throughout the measurement. Glass windows in the measuring chamber made it possible to microscopically observe the membrane in transmission.

An electric field of 200 V/cm was applied and was switched off again after a time $t_e$=5 min. Immediately after switching off monoclonal primary antibodies against the cytoplasmic binding epitope of band-3 protein (Mouse IgG, Sigma) and glycophorine (Isotope IgG1, Kappa, Dako) were flushed into the measuring chamber and incubated for 5 min. The measuring chamber was then rinsed with ten times its own volume quantity with buffer A in order to remove non-bound antibodies. Then, for the two primary antibodies, specific fluorescence-labelled, secondary antibodies (Monoclonal Antibody (Rat) to Mouse Isotype IgG1 Kappa, with FITC-Label and Goat Anti Mouse IgG with TRITC-Label) were flushed into the cell and the incubation and flushing procedure was repeated in accordance with the above protocol. The time between the flushing in of the protein-specific antibodies and the washing out of the remaining, fluorescence-labelled secondary antibodies was max 30 minutes. The slide with membrane and the antibodies bound thereon were then dried at 50° C. and under a slight vacuum, in order to prevent a further (thermally caused) diffusion of the proteins, with antibodies, following the switching off of the electric fields. The distribution of the antibodies on the slide surface was then investigated in fluorescence microscopic manner. The use of edge filters made it possible to distinguish the antibody fluorescence of the secondary antibodies bound to glycophorine or band-3. By means of digital image processing a densitogram was recorded of the fluorescence intensity distribution along the randomly selected 10 µm wide connecting line between the two electrodes.

The tests were repeated for a different time of switching on the electric field ($t_e$=5, 15, 30, 60 min.) with an unchanged field strength for in each case new membrane samples prepared in accordance with 2.1. Analysis of the measured results (densitograms as a function of $t_e$) took place through the determination of the positions $X_{min}$ of the fluorescence minimum and $X_{max}$ of the fluorescence maximum along the line connecting the two electrodes in the x-direction (cf. FIG. 1). These coordinates were plotted for $X_{min}$ in a graph as a function of $t_e$ and are shown in FIG. 3. The position $X_{min}$=0 mm corresponds to one edge of the slide and $X_{min}$=40 mm to the opposite edge. It is clear that both proteins have moved through the electric field towards the electrodes and that the drift rate caused by this field was different for the two proteins.

Control measurements were carried out for an identically prepared system according to $t_e$=60 min, but where the electric field strength was only 5 V/cm. In this case it was not possible to prove any significant shift of the two proteins using the above-described procedure.

3.2. Membrane of the Sarcoplasmic Reticulum (SR)

The test setup and performance were the same as in 3.1, but measurement took place with the SR-membrane prepared under 2.2 and using buffer C instead of buffer B. In addition, in this case specific, primary antibodies for the cytoplasmic binding epitope of calcium-ATP-ase of SR (monoclonal Mouse IgG 3-911, 912 (Dianova)) were used for flushing in following the switching off of the electric field. The antibody distribution was detected by fluorescence-labelled secondary antibodies (Monoclonal Antibody (Rat) to Mouse Isotype IgG1 Kappa, with FITC-Label). The evaluation of $X_{min}$ as a function of $t_e$ revealed a clear migration of the calcium-ATP-ase towards the electrode (FIG. 4). The position $X_{min}$=0 mm corresponds to one edge of the slide and $X_{min}$=40 mm to the opposite edge.

Control measurements identical to those described in 3.1, but here again there was no protein displacement for a field strength of only 5 V/cm.

4. Electrophoresis (Two-Dimensional)

These tests were performed with a test setup identical to that described in 3. The only difference was that in these experiments additionally the electrodes shown in FIG. 1 were controlled in the transverse direction (transverse electrodes, y-direction), permitting a build-up of a second electric field with a field direction perpendicular to the first field (longitudinal electrodes, x-direction). These tests were performed with the SR-membranes described under 3.2. Firstly the test was performed completely identically to what was described in 3.2 by means of longitudinal electrodes at $t_e$=60 min as if the second pair of electrodes (transverse electrodes) was not present. Following this time, the calcium-ATP-ase present in the membrane had largely concentrated in the environment of one of the two longitudinal electrodes, whereas it could no longer be detected at the others (cf. 3.2). The polarity of the longitudinal electrodes was now reversed and simultaneously the transverse electrodes were switched on (voltage of both electrode pairs 200 V/cm). Following a time $t_e$=60 min, both electrodes were simultaneously switched off. Then the method described in 3.1 and 3.2 was carried out in identical manner for visualizing the calcium-ATP-ase by flushing in the specific antibody, as well as the fluorescence-labelled, secondary antibody and subsequent washing out of non-bound antibodies, the support with the membrane and antibodies was dried and was investigated in fluorescence-microscopic manner.

The investigation revealed a substantial localization of the protein in one corner or angle of the square fixed by the four electrodes. The size of the protein spot was established as 50 to 100 µm. This result is a significant difference compared with the one-dimensional electrophoresis described in 3.2, where after the same time the protein was relatively homogeneously distributed along one of the two longitudinal electrodes. This proves that by two-dimensional electrophoresis, a membrane protein can be so manipulated within the planar membrane on the slide that it is finally concentrated at a location defined by two dimensions.

What is claimed is:

1. A method for separating membrane proteins that extend through a membrane or are partially inserted in a membrane, the method comprising:
   performing a first stage of the method by chemically modifying a surface of a fixed phase support material into a state that allows adsorption of a biological membrane thereon to form a membrane plane;
   performing a second stage of the method by adsorbing a biological membrane containing membrane proteins onto the chemically modified surface of the fixed phase support material in such a way as to form a membrane plane with the membrane proteins substantially retaining their capacity to diffuse into the membrane plane; and
   performing a third stage of the method by applying suitable electric fields to the adsorbed membrane to cause electrophoretic movement of the membrane proteins in the membrane plane leading to their separation in one or two dimensions.

2. The method of claim 1, wherein said support material has a planar surface and the chemical modification with subsequent adsorption of a biological membrane and electrophoresis is carried out on said planar surface.

3. The method of claim 2, wherein said support material comprises silicate compounds, particularly glass, ceramics, polymers, metals or semiconductor materials.

4. The method of claim 2, wherein the surface is microstructured or nanostructured in planned manner by technical processes.

5. The method of claim 1, wherein said fixed phase support material comprises silicate compounds, particularly glass, ceramics, polymers, metals or semiconductor materials.

6. The method of claim 5, wherein the fixed phase support material is microstructured or nanostructured in planned manner by technical processes.

7. The method of claim 1, wherein the chemical modification takes place by the method stages comprising:
   a) functionalizing the surface with molecules for forming a substantially either hydrophobic or hydrophilic layer; and
   b) adsorption or chemisorption of molecules interacting with this layer.

8. The method of claim 7, wherein said functionalization of the surface is carried out by the application of amino functions, epoxy functions, halogen alkyl functions and/or thio functions.

9. The method of claim 7, wherein silanes, mercaptans and/or disulphides, particularly alkyl disulphides are used for said functionalizing.

10. The method of claim 7, wherein polymers, particularly polyelectrolytes, polyampholytes, preferably proteins, and/or polyzwitter ions are used as said interacting molecules.

11. The method of claim 7, wherein polystyrene sulphonate and/or poly(styrene-co-maleic anhydride) are used as said interacting molecules.

12. The method of claim 1, wherein the chemical modification comprises the following method stages:
   a) functionalizing the surface of the fixed phase support material, and/or
   b) adsorption or chemisorption of interacting molecules, and
   c) adsorption or chemisorption of further molecules able to interact with the molecules used in stage b).

13. The method of claim 12, wherein said functionalizing of the surface of the fixed phase support material is carried out by the application of amino functions, epoxy functions, halogen alkyl functions and/or thio functions.

14. The method of claim 12, wherein silanes, mercaptans and/or disulphides, particularly alkyl disulphides are used for said functionalizing.

15. The method of claim 12, wherein polymers, particularly polyelectrolytes, polyampholytes, preferably proteins, and/or polyzwitter ions are used as said interacting molecules.

16. The method of claim 12, wherein polystyrene sulphonate and/or poly(styrene-co-maleic anhydride) are used as said interacting molecules.

17. The method of claim 1, wherein the surface is microstructured or nanostructured in planned manner by technical processes.

18. The method of claim 1, wherein the biological membrane is obtained by fusion of vesicles of said biological membrane on said modified surface.

19. The method of claim 18, wherein production of the vesicles of said biological membrane takes place by urtrasonic treatment or by the pressing of the biological membrane under increased pressure through nanoporous filters and/or through nozzles.

20. The method of claim 18, wherein the biological membrane essentially comprises organelles of eukaryotic cells.

21. The method of claim 1, wherein the biological membrane essentially comprises organelles of eukaryotic cells.

22. The method of claim 1, wherein said electrophoresis is performed by at least one pair of electrodes, which can produce an electric field, which is essentially located in the plane of said membrane.

23. The method of claim 22, wherein the electrodes are operated with d.c. voltage or a.c. voltage.

24. The method of claim 22, wherein the electrodes are used for the release of electric field pulses.

25. The method of claim 22, wherein the electrode pairs are simultaneously or alternately supplied with power.

26. The method of claim 22, wherein more than one pair of electrodes is used for electrophoresis and are able to produce electric fields in any direction in space.

27. The method of claim 26, wherein the electrode pairs are simultaneously or alternately supplied with power.

28. The method of claim 26, wherein the electrodes are operated with d.c. voltage or a.c. voltage.

29. The method of claim 26, wherein the electrodes are used for the release of electric field pulses.

30. The method of claim 1, wherein the achieved separation of the membrane proteins is visualized or detected by fluorescence, particularly single photon detection methods, by luminescence or by radioactive labeling.

31. The method of claim 1, wherein the attained separation of the membrane proteins is detected or analyzed by mass spectrometric methods, particularly MALDI-TOF.

32. The method of claim 1, comprising the further method stage of visualizing the separation of previously radioactively labeled membrane proteins using multiple photon detection technology (MPD).

* * * * *